(12) United States Patent
Travish et al.

(10) Patent No.: US 12,324,690 B2
(45) Date of Patent: Jun. 10, 2025

(54) METHOD OF OBTAINING X-RAY IMAGES

(71) Applicant: ADAPTIX LTD, Begbroke (GB)

(72) Inventors: Gil Travish, Begbroke (GB); Mark Evans, Begbroke (GB)

(73) Assignee: ADAPTIX LTD, Begbroke (GB)

( * ) Notice: Subject to any disclaimer, the term of this patent is extended or adjusted under 35 U.S.C. 154(b) by 285 days.

(21) Appl. No.: 17/740,840

(22) Filed: May 10, 2022

(65) Prior Publication Data

US 2022/0265225 A1    Aug. 25, 2022

Related U.S. Application Data

(63) Continuation of application No. PCT/GB2020/052880, filed on Nov. 12, 2020.

(30) Foreign Application Priority Data

Nov. 12, 2019 (GB) ...................................... 1916450

(51) Int. Cl.
*A61B 6/02* (2006.01)
*A61B 6/40* (2024.01)
*A61B 6/46* (2024.01)

(52) U.S. Cl.
CPC ............ *A61B 6/025* (2013.01); *A61B 6/4007* (2013.01); *A61B 6/405* (2013.01); *A61B 6/4085* (2013.01); *A61B 6/466* (2013.01)

(58) Field of Classification Search
None
See application file for complete search history.

(56) References Cited

U.S. PATENT DOCUMENTS 6,028,910 A * 2/2000 Kirchner ............. G01N 23/044
378/22
6,324,249 B1 * 11/2001 Fazzio ................. G01N 23/044
378/22

(Continued)

FOREIGN PATENT DOCUMENTS

EP      3533396      9/2019
WO      2009012453   1/2009

OTHER PUBLICATIONS

UKIPO, Search Report in corresponding GB application GB1916450.8, May 13, 2020.

(Continued)

*Primary Examiner* — Marcus H Taningco
*Assistant Examiner* — Djura Malevic
(74) *Attorney, Agent, or Firm* — Alley IP

(57) ABSTRACT

An x-ray imaging apparatus comprises a panel including individually energisable x-ray emitters, a detector and a processor, wherein the emitters and detector remain relatively stationary. The first set of x-ray emitters of the panel is energised to direct x-rays at the first object and surrounding area. The detector detects x-rays passing through the first object and surrounding area. Detected x-rays are processed to create a first x-ray image of the first object and surrounding area. A region of interest is selected from the first image which is smaller than the image of the first object and surrounding area. A second set of x-ray emitters of the panel is energised to direct x-rays at the region of interest. The detector detects x-rays passing through the region of interest. Detected x-rays are processed to create images of the region of interest to obtain tomosynthesis data showing structure of the region of interest.

5 Claims, 4 Drawing Sheets

(56) References Cited

U.S. PATENT DOCUMENTS

| | | | | |
|---|---|---|---|---|
| 7,873,146 | B2* | 1/2011 | Okunuki | H01J 35/18 378/124 |
| 8,149,987 | B2* | 4/2012 | Ogura | A61B 6/469 378/115 |
| 8,220,993 | B2* | 7/2012 | Takahashi | A61B 6/4007 378/92 |
| 8,744,041 | B2* | 6/2014 | Smith | A61B 6/467 378/37 |
| 8,873,706 | B2* | 10/2014 | Ogura | A61B 6/4007 378/115 |
| 9,008,263 | B2* | 4/2015 | Jang | A61B 6/482 378/98.12 |
| 9,408,577 | B2* | 8/2016 | Tamura | A61B 6/4007 |
| 9,579,526 | B2* | 2/2017 | Kunz | A61B 6/4429 |
| 10,076,290 | B2* | 9/2018 | Lee | A61B 6/4405 |
| 10,585,206 | B2* | 3/2020 | Bendahan | G01V 5/22 |
| 10,610,175 | B2* | 4/2020 | Maurer, Jr. | A61B 6/4447 |
| 10,901,112 | B2* | 1/2021 | Morton | A61B 6/4488 |
| 10,976,271 | B2* | 4/2021 | Morton | G01N 23/20083 |
| 11,020,066 | B2* | 6/2021 | Butani | A61B 6/4208 |
| 11,076,820 | B2* | 8/2021 | Smith | A61B 6/4007 |
| 11,212,902 | B2* | 12/2021 | De Antonis | H05G 1/56 |
| 11,298,095 | B2* | 4/2022 | Zhao | A61B 6/5235 |
| 11,558,950 | B2* | 1/2023 | Fritz | H05G 1/22 |
| 11,602,315 | B2* | 3/2023 | Zhao | A61B 6/5282 |
| 11,740,922 | B2* | 8/2023 | Johnsen | G06F 9/45558 718/1 |
| 11,778,717 | B2* | 10/2023 | Jafari | H01J 35/065 378/113 |
| 11,796,711 | B2* | 10/2023 | Morton | H05G 1/70 |
| 11,844,640 | B2* | 12/2023 | Zhao | A61B 6/5217 |
| 11,950,944 | B2* | 4/2024 | Zhou | A61B 6/4417 |
| 12,004,885 | B2* | 6/2024 | Zhao | A61B 6/4021 |
| 12,058,800 | B2* | 8/2024 | Park | H05G 1/58 |
| 2009/0022264 | A1* | 1/2009 | Zhou | A61B 6/025 378/5 |
| 2009/0103679 | A1* | 4/2009 | Jabri | A61B 6/06 378/70 |
| 2009/0225934 | A1* | 9/2009 | Hugg | A61B 6/469 378/20 |
| 2009/0316860 | A1* | 12/2009 | Okunuki | H01J 35/065 378/141 |
| 2010/0195796 | A1* | 8/2010 | Takahashi | A61B 6/4007 378/92 |
| 2012/0008735 | A1* | 1/2012 | Maurer | A61B 6/488 378/5 |
| 2012/0163533 | A1* | 6/2012 | Ogura | A61B 6/025 378/62 |
| 2015/0016586 | A1* | 1/2015 | Maurer, Jr. | G06T 7/0014 378/5 |
| 2018/0067061 | A1* | 3/2018 | Butani | G01N 23/046 |
| 2018/0289348 | A1* | 10/2018 | Cox | A61B 6/4078 |
| 2019/0388050 | A1* | 12/2019 | Lee | A61B 6/54 |
| 2022/0265225 | A1* | 8/2022 | Travish | A61B 6/4007 |

OTHER PUBLICATIONS

WIPO, International Search Report and Written Opinion in corresponding PCT application PCT/GB2020/052880, Feb. 25, 2021.

J, Zhang et al, "A multi-beam x-ray imaging system based on carbon nanotube field emitters," Medical Imaging 2006.

JPO, Search Report in corresponding JP application 2022-526845, May 16, 2024.

* cited by examiner

METHOD OF OBTAINING X-RAY IMAGES

RELATED APPLICATIONS

This application claims the benefit under 35 U.S.C. § 120, and is a continuation, of co-pending International Application PCT/GB2020/052880, filed Nov. 12, 2020 and designating the US, which claims priority to GB Application 1916450.8, filed Nov. 12, 2019, such GB Application also being claimed priority to under 35 U.S.C. § 119. These GB and International applications are incorporated by reference herein in their entireties.

FIELD

The present invention relates generally to a method of obtaining x-ray images and apparatus arranged to operate according to the method and finds particular, although not exclusive, utility in reducing dosage without undue loss of clarity in the images.

BACKGROUND

Although x-ray images are desirable for assessing medical conditions of patients, dosage levels need to be controlled to avoid undesirable side-effects. This is typically effected by the use of collimators which are effectively 'shutters' which restrict the exposed area of the patient to a defined square or rectangle. This is effective, but sub-optimal as often the tissue within the region exposed that absorbs a significant proportion of the x-ray (i.e. incurs most 'dose') is not that which is of clinical interest. For instance, in a normal chest x-ray, a very frequent diagnostic procedure predominantly used to examine lung tissue, it is often the surrounding tissue (the liver, shoulders, the neck) which absorbs a significant proportion of the x-ray. In this instance, surrounding organs will incur dose despite the fact they are not of diagnostic interest.

Importantly, the 'dose cost' of extending the collimated field is less than the dose cost of re-performing an examination that did not acquire a complete image of the region of clinical interest. As a result, radiographers are incentivized to have a material margin around the region of clinical interest which means that regions not of clinical interest are exposed to x-ray radiation.

SUMMARY

It is desirable, therefore, to be able to optimise the use of x-ray flux within a diagnostic imaging procedure to minimise dosage but produce clear images.

In a first aspect, the present invention provides a method of obtaining x-ray images of a first object obscured by a second object; the method comprising the steps of:
  providing an x-ray imaging apparatus comprising a panel including an array of individually energisable x-ray emitters, a detector and a processor, wherein the array and the detector remain stationary relative to one another, and wherein the array and the detector remain stationary relative to the second object;
  energising a first set of x-ray emitters of the panel over a first period of time and directing the x-rays at the first object and surrounding area;
  using the detector to detect the x-rays after passing through the first object and surrounding area;
  processing the detected x-rays to create a first x-ray image of the first object and surrounding area;
  selecting a region of interest from the first x-ray image which is smaller than the first x-ray image of the first object and surrounding area;
  energising a second set of x-ray emitters of the panel over a second period of time and directing the x-rays at the region of interest;
  using the detector to detect the x-rays after passing through the region of interest;
  processing the detected x-rays to create a set of x-ray images of the region of interest to obtain tomosynthesis data showing the structure of the region of interest.

The panel may be a Flat Panel X-ray Source (FPS) and the detector may be a Flat Panel X-ray Detector (FPD). The two devices may work in conjunction along with the processor which acts as an 'Acquisition Workstation' to analyse the output of the FPD and reconstruct multiple frames in to a 3D model which can be exported (often via a Picture Archiving and Communication System ('PACS')) to a 'Visualization Workstation' on which a clinician may review the images using viewing software.

The second object may be substantially stationary relative to the array and detector. For example, if the first object is a moving organ (such as a pair of lungs), they may be temporarily stilled by the patient holding their breath. The term stationary may include relatively minor movements such as due to blood flow or the effect of the nearby heart.

The first object may be a lung. The second object may be the human body within which the lung is located.

The first x-ray image allows for the region of interest to be chosen minimising the area which will receive the second set of x-rays. The first x-ray image may be considered to be a "scout-scan".

The region of interest may be smaller than the image of the first object and surrounding area due to the selection of emitters being energised during the method, rather than by use of a collimator, or other "blanking" means. Moreover, the second set of x-ray emitters may be selected so that the area of x-ray incidence, on the first object, from this second set, when energised, is smaller than the area of incidence of x-rays thereon from the first set of x-ray emitters, when energised.

The selection of the region of interest may be automatically made by the apparatus by reference to a set of rules. In this regard, the set of rules may be determined from historical records, such as those recorded in a database. The set of rules may be created by humans or by computer-based algorithms such as those used by artificial intelligence.

The selection of the region of interest may be made by the operator. In other words, the operator, who may be the clinician, may manually choose the region of interest upon viewing the first image. Alternatively, or additionally, the region of interest may be based on an earlier diagnostic scan (such as x-ray, CT, DT or MRI). Alternatively, or additionally, the region of interest may be made by the operator in conjunction with suggestions made by the apparatus by reference to the set of rules.

The set of rules may be based on information concerning typical shapes of objects for x-ray imaging. For example, the typical shapes of human lungs. In other words, because a particular organ has a typical shape, the region of interest may be definable based on that typical shape in conjunction with the boundaries of that particular organ as determined from the first x-ray image. In this regard, the processor may be configured to determine at least some portions of the actual boundary of the target, such as an organ, from the first x-ray image. It may be able to suggest where the boundary lies in the portion(s) not covered by the x-rays emitted in the first period of time.

The set of rules may be based on information concerning dose effect of x-rays on x-ray targets. For instance, each organ may react differently to the same level of dosage and thus each organ may have a maximum safe limit of dosage. Accordingly, it may be considered acceptable to use higher dosages with some targets compared to others. The processor may be configured to determine dosage rates based on information concerning the target, for example, the name of the organ. Such information may be given to the processor by an operator, and/or be determined by the processor from the, or a different, set of rules, based on the first image.

The x-rays may be emitted from each emitter in a cone shape having an angle of divergence in the range 15 to 20 degrees. Other angles are contemplated. X-ray collimators may be employed with each emitter to create the required cone shape. The angle of emission may be different for each emitter, or they may all have the same angle of emission. Another possibility is that some emitters have one angle and some emitters have another angle, and so on. In this way, the process may be adapted as required. For instance, small circles of x-rays at the detector, with commensurately relatively narrow emission angles may be used for shaping the overall area of coverage, whereas, larger circles of x-rays at the detector, with commensurately relatively wider emission angles may be used for producing effective tomosynthesis.

The number of emitters energised in the first time period may be fewer than the number of emitters energised in the second time period.

The emitters energised in the second time period may be energised in temporal separation to ensure over-sampling and to allow 3D tomosynthesis image reconstruction of the region of interest.

The emitters energised in the first time period may be energised in temporal separation.

The method may be used in a diagnostic imaging procedure. The method may exclude therapeutic radiation treatment.

In a second aspect, the invention provides an x-ray imaging apparatus arranged to operate according to the first aspect.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION

Figure 1:
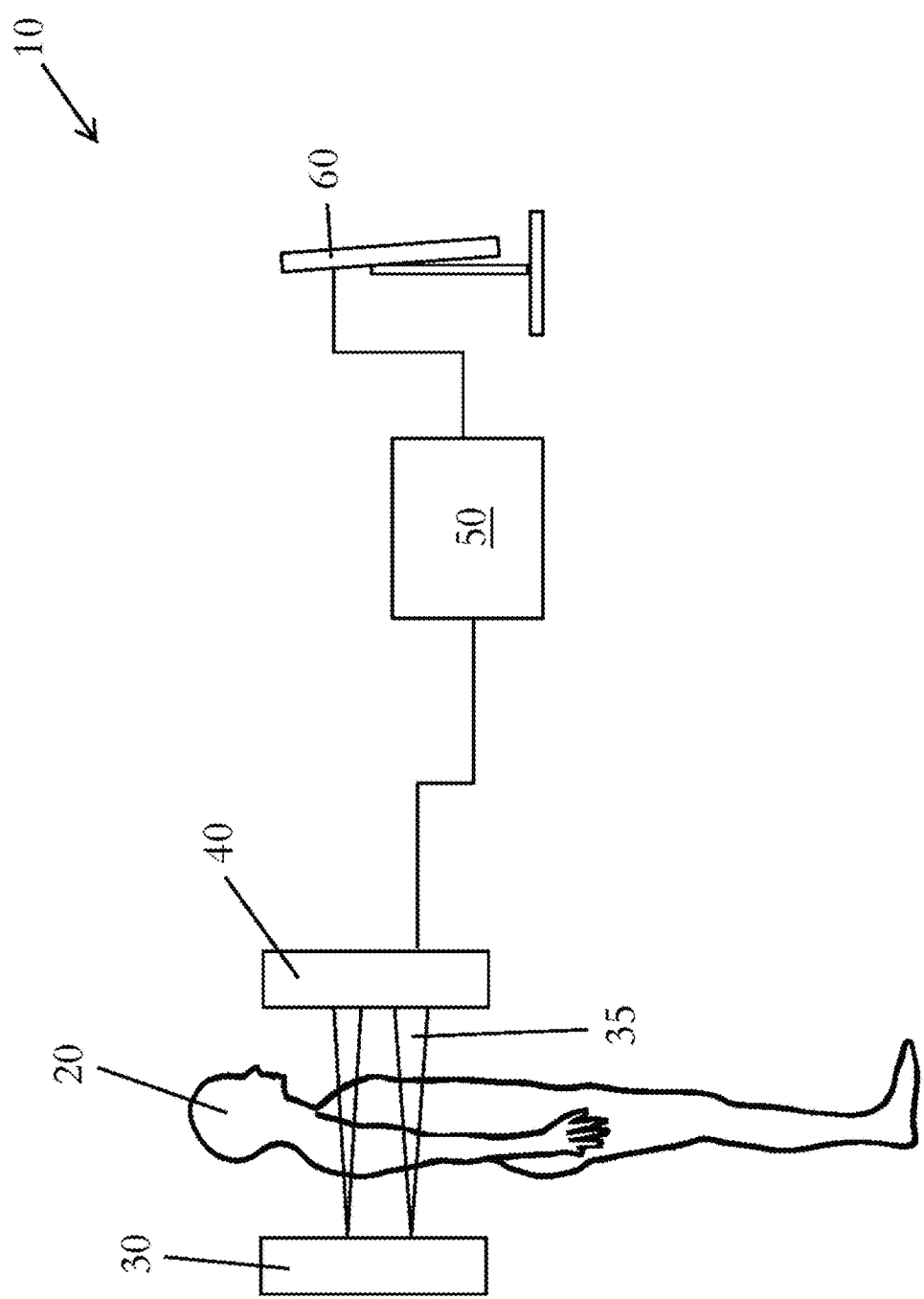
FIG. 1 is schematic view of x-ray apparatus in use.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein. Likewise, method steps described or claimed in a particular sequence may be understood to operate in a different sequence.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any one embodiment or aspect of the invention may be combined in any suitable manner with any other particular feature, structure or characteristic of another embodiment or aspect of the invention, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The use of the term "any" may mean "all" and/or "each" in certain circumstances.

The principles of the invention will now be described by a detailed description of at least one drawing relating to exemplary features. It is clear that other arrangements can be configured according to the knowledge of persons skilled in the art without departing from the underlying concept or technical teaching, the invention being limited only by the terms of the appended claims.

In FIG. 1 an x-ray apparatus 10 is shown including a flat panel emitter array 30, emitting x-rays 35 through the chest of a patient 20. The x-rays are detected by a detector panel 40 opposite the emitter array 30.

The resultant data is sent to a processor 50 where it may be processed to create images viewable on a screen 60.

Only two cones of x-rays 35 are shown, however, it is to be understood that in use, more x-ray cones may be emitted simultaneously and/or consecutively as required during the process.

To obtain an x-ray image of only an area of interest, thus excluding other areas, the firing of the x-ray emitters may be modified according to the clinical region of interest such that only the clinical region of interest receives a full diagnostic dose.

This may be achieved by firstly defining the area of diagnostic interest. This may be achieved by conducting a 'scout scan' where a first subset of emitters is fired sequentially in order to minimally cover the field of view.

Figure 2:
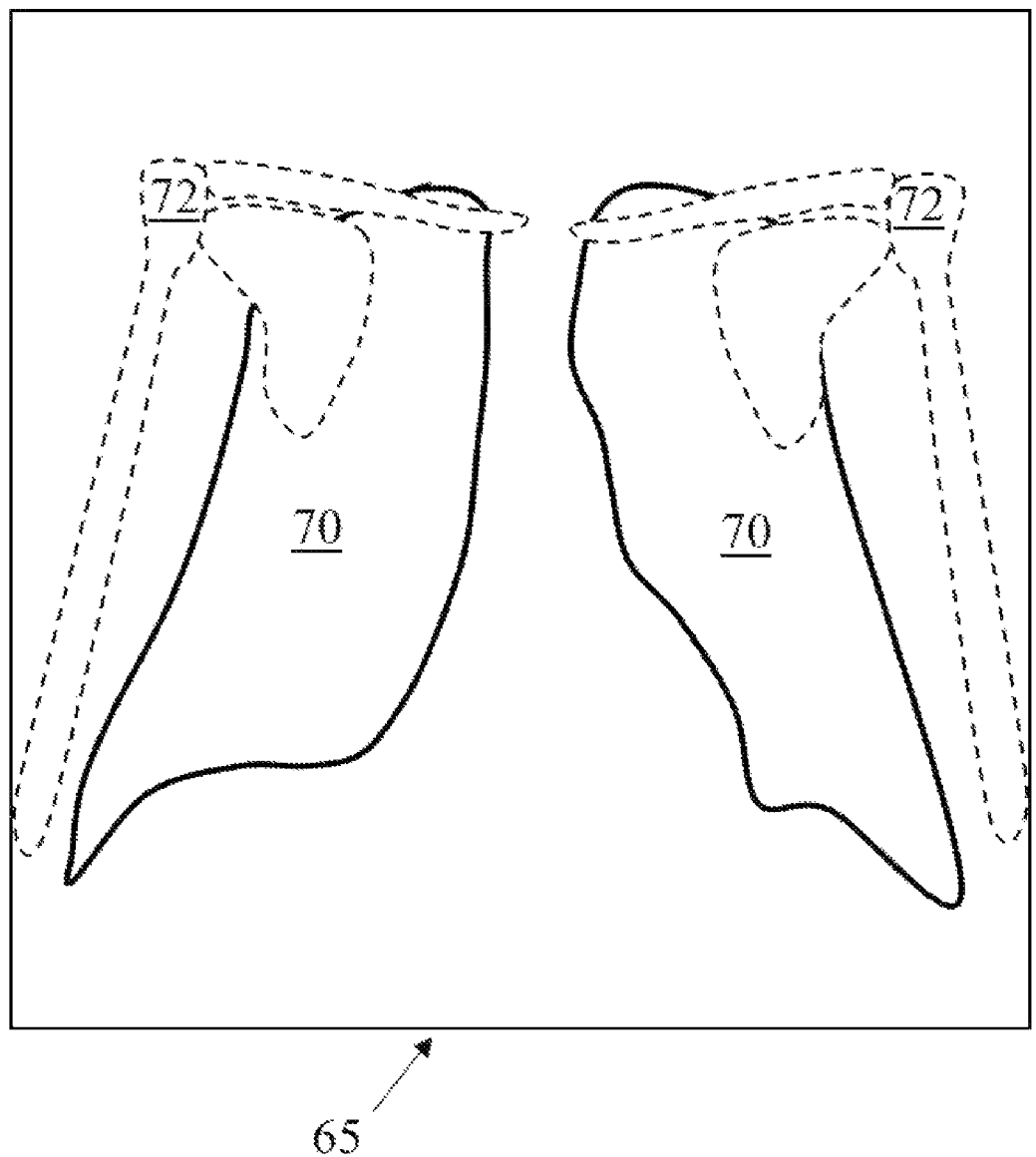
FIG. 2 is a schematic view of an x-ray image of a pair of lungs and surrounding area.

FIG. 2 shows an x-ray image 65 of a portion of a patient's chest created by subjecting that area to this first subset of x-rays. The lungs 70 are visible as well as schematic representations of various bones, some of which form the shoulders 72. The image will likely include other anatomic parts of the patient's chest but are not shown. The area of the x-ray image is bounded by the box 65, however, this is representational only and it may be smaller than this.

Within this field of view, the region of clinical interest can be found manually and/or automatically by image segmentation. An example method of automatic segmentation would be based on the fact that lungs are mostly air so appear very dark on an x-ray. A thresholding method may be employed to segment all dark areas.

The lungs are a familiar shape so the thresholded dark areas may be pattern matched to a template. This matching may occur manually and/or automatically. Different templates may be used for images taken from the back (Posterior-Anterior view), and for lateral images taken from the side.

Figure 3:
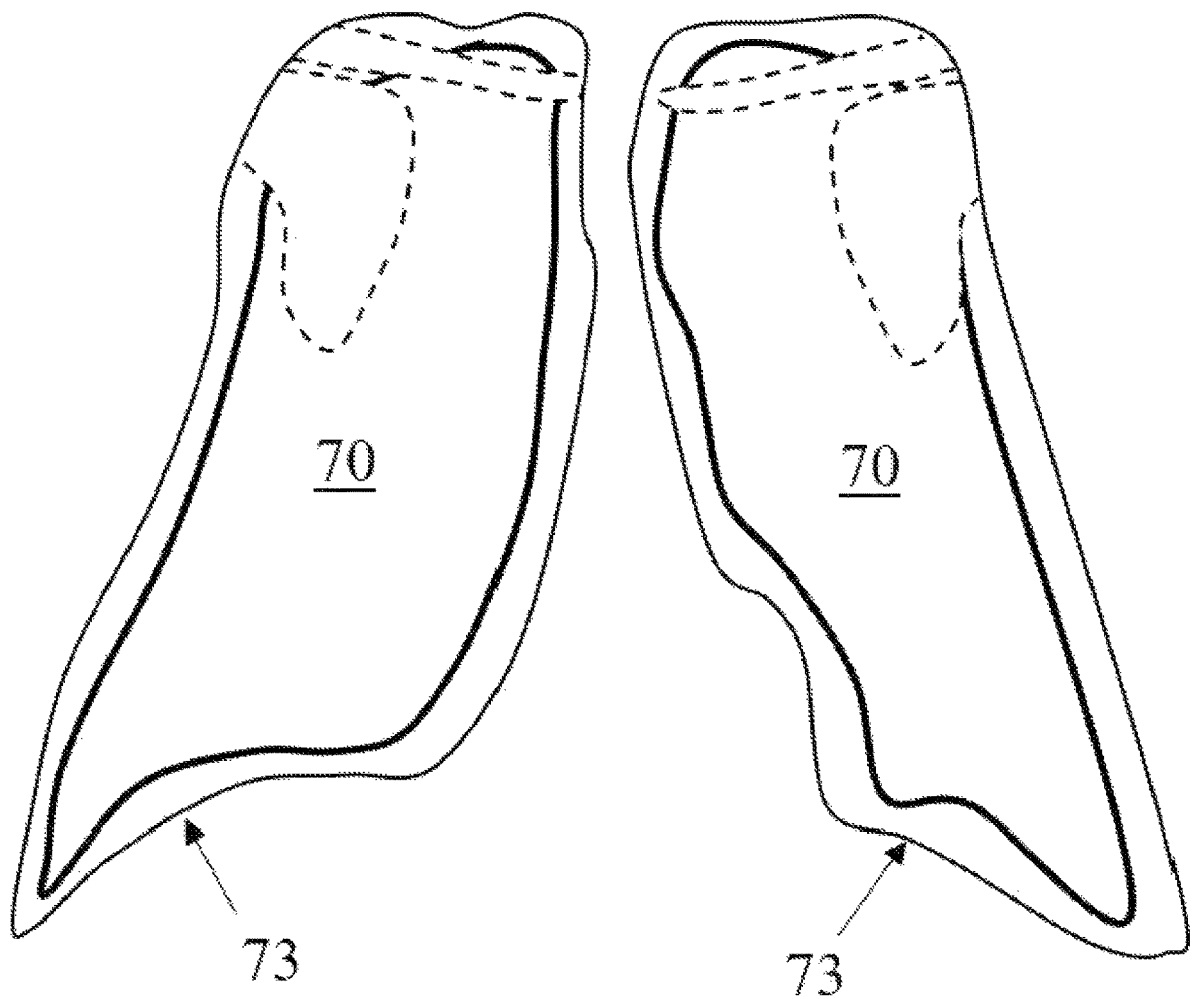
FIG. 3 is a schematic view of the pair of lungs of FIG. 2 having had an outline superimposed thereon.

FIG. 3 shows how a perimeter 73 has been defined around each lung 70. The perimeter is slightly larger than each lung 70 so as to include a margin around each. This may be considered as the first step in defining the final region of interest, and may occur automatically and/or with human operator input.

Figure 4:
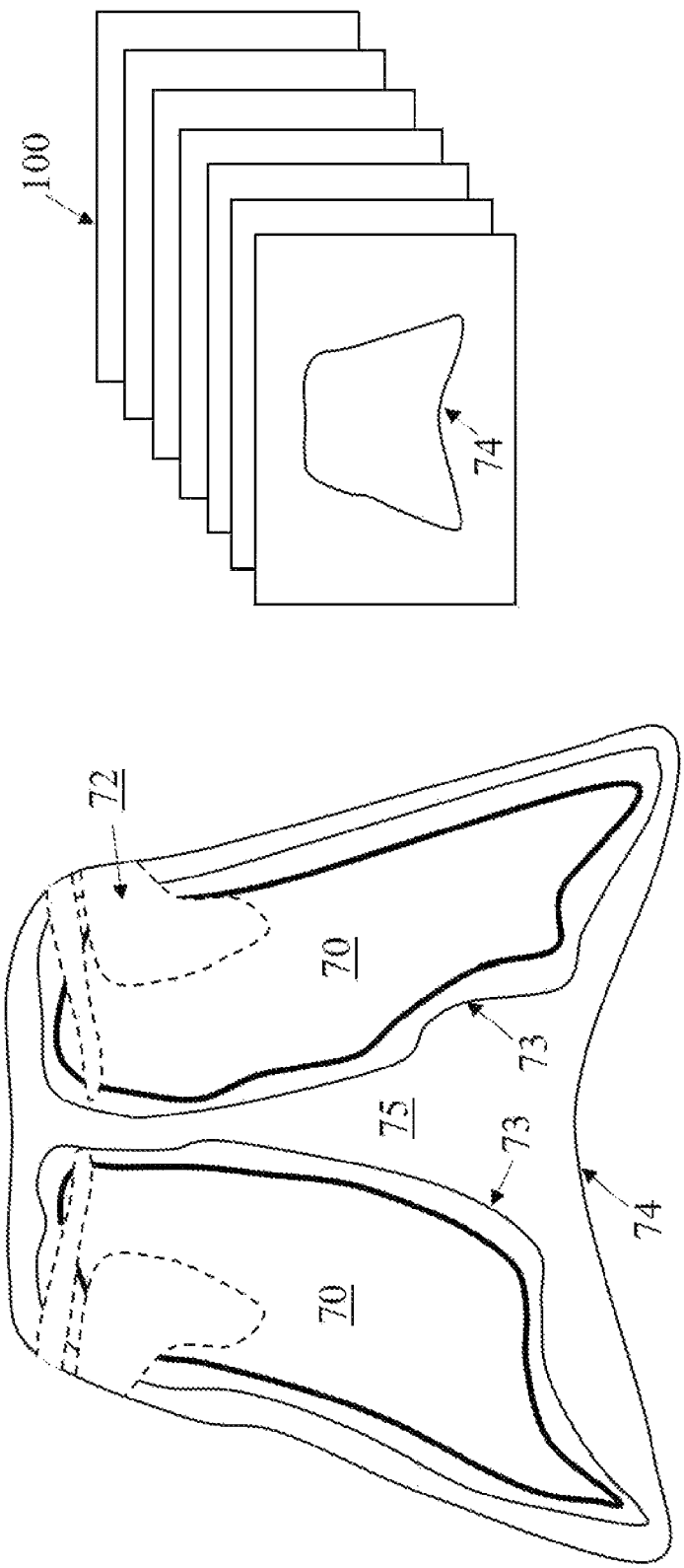
FIG. 4 is a schematic view of the pair of lungs of FIG. 3 together with a smaller surrounding area having been subjected to a second set of x-rays to obtain tomosynthesis data showing the structure of the lungs.

In FIG. 4, the final region of interest is shown as an outer perimeter 74 surrounding each marginal boundary 73 defined above. This outer perimeter 74 includes a further marginal area around, and larger than, each marginal boundary 73 around each lung and the mediastinum area 75 between the two lungs 70.

After the final region of interest has been subjected to the second set of x-rays the resultant images may be processed using known processing techniques to create a 3D tomosynthesis model of the lungs. This information may be presented in the form of slices 100 such that a clinician may view the lungs at various depths through their thickness.

Some of the bones 72 are still within this region of interest 74, however, if the x-rays images are taken from in front of the patient the shoulder bones behind may not reduce the effectiveness of the resultant images too much. Also, it is to be noted that the patient may be asked to move their arms into certain positions, such as by hugging the detector, prior to the x-rays being emitted to reduce the presence of the bones in the region of interest. Most of the shoulder bones shown in the example have been excluded by this method but some bones, which are not of clinical interest 72, may still cast a shadow over part of this region of interest 74 due to normal anatomy and patient positioning.

Although various margins have been discussed above with respect to FIGS. 3 and 4 and the lungs, it is to be understood that the method may minimise or exclude margins. Also, although the definition of the final region of interest has been discussed above with respect to FIGS. 3 and 4 as having two stages, it is to be understood that the definition of this region may be effected in a single step or indeed in more than two steps. This may be dependent on the part of the body which is of interest.

For full digital tomosynthesis acquisition, an acquisition workstation (the apparatus) may define which individual emitters may be fired to adequately cover the selected region of clinical interest. For adequate tomosynthesis this may involve firing emitters that illuminate the region of interest plus a small margin around it. Emitters illuminating areas of the field of view away from the region of interest may not be fired, thus saving dose.

It is to be understood that an image produced from the first subset of x-rays may be used with the images from the second sets of x-rays.

Although this method and apparatus have been described with respect to patients and the derivation of medical information, it is to be understood that they could be used with respect to other objects, for instance, the analysis of luggage.

The invention claimed is:

1. A method of obtaining x-ray images of a first object obscured by a second object; the method comprising the steps of:
   a) providing an x-ray imaging apparatus comprising a panel including an array of individually energisable x-ray emitters, a detector and a processor, wherein the array and the detector remain stationary relative to one another, and wherein the array and the detector remain stationary relative to the second object;
   b) energising a first set of x-ray emitters of the panel over a first period of time and directing the x-rays at the first object and surrounding area;
   c) using the detector to detect the x-rays after passing through the first object and surrounding area;
   d) processing the detected x-rays to create a first x-ray image of the first object and surrounding area;
   e) selecting, by an operator in conjunction with suggestions made by the apparatus by reference to a set of rules, a region of interest from the first x-ray image which is smaller than the first x-ray image of the first object and surrounding area;
   f) energising a second set of x-ray emitters of the panel over a second period of time and directing the x-rays at the region of interest, wherein the emitters energised in the second time period are energised in temporal separation to ensure over-sampling and allow 3D tomosynthesis image reconstruction of the region of interest;
   g) using the detector to detect the x-rays after passing through the region of interest;
   h) processing the detected x-rays to create a set of x-ray images of the region of interest to obtain tomosynthesis data showing the structure of the region of interest, wherein the number of emitters energised in the first time period is fewer than the number of emitters energised in the second time period.

2. The method of claim 1, wherein the set of rules is based on information about typical shapes of x-ray targets.

3. The method of claim 1, wherein the set of rules is based on information about dose effect of x-rays on x-ray targets.

4. The method of claim 1, wherein the x-rays are emitted from each emitter in a cone shape having an angle of divergence in the range 15 to 20 degrees.

5. An x-ray imaging apparatus comprising a panel including an array of individually energisable x-ray emitters, a detector and a processor, wherein the array and the detector are arranged to remain stationary relative to one another, in use, and wherein the array and the detector are arranged to remain stationary relative to the second object, in use;
   a) the apparatus arranged to energise a first set of x-ray emitters of the panel over a first period of time and to direct the x-rays at the first object and surrounding area;
   b) the detector arranged to detect the x-rays after passing through the first object and surrounding area;
   c) the processor arranged to process the detected x-rays to create a first x-ray image of the first object and surrounding area;
   d) the processor arranged to make suggestions, by reference to a set of rules, enabling an operator in conjunction with the suggestions made by the processor to select a region of interest from the first x-ray image which is smaller than the first x-ray image of the first object and surrounding area;
   e) the apparatus arranged to energise a second set of x-ray emitters of the panel over a second period of time and to direct the x-rays at the region of interest, wherein the emitters energised in the second time period are energised in temporal separation to ensure over-sampling and allow 3D tomosynthesis image reconstruction of the region of interest;
   f) the detector arranged to detect the x-rays after passing through the region of interest;
   g) the processor arranged to process the detected x-rays to create a set of x-ray images of the region of interest to obtain tomosynthesis data showing the structure of the region of interest, wherein the number of emitters energised in the first time period is fewer than the number of emitters energised in the second time period.

* * * * *